US007515676B2

(12) United States Patent
Zamyatin

(10) Patent No.: US 7,515,676 B2
(45) Date of Patent: Apr. 7, 2009

(54) METHOD, APPARATUS, AND COMPUTER PROGRAM PRODUCT FOR SINOGRAM COMPLETION

(75) Inventor: Aleksandr A. Zamyatin, Buffalo Grove, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 297 days.

(21) Appl. No.: 11/412,950

(22) Filed: Apr. 28, 2006

(65) Prior Publication Data

US 2007/0253523 A1 Nov. 1, 2007

(51) Int. Cl.
*A61B 6/03* (2006.01)
(52) U.S. Cl. .......................................... 378/4; 378/901
(58) Field of Classification Search ...................... 378/4, 378/901; 382/128–131
See application file for complete search history.

(56) References Cited

U.S. PATENT DOCUMENTS

| 6,529,575 | B1* | 3/2003 | Hsieh ............................ 378/4 |
| 2003/0107770 | A1* | 6/2003 | Klatchko et al. ........... 358/3.21 |
| 2006/0233459 | A1* | 10/2006 | Lange et al. ................. 382/276 |

OTHER PUBLICATIONS

Bertram et al., Directional Interpolation of Sparsely Sampled Conebeam CT Sinogram Data, 2004, IEEE, Biomedical Imaging: Nano to Micro, vol. 1, pp. 928-931.*

R. Chityala, et al. "Artifact Reduction in Truncated CT Using Sinogram Completion", Proceedings SPIE Medical Imaging: Image Processing 5747, Apr. 2005, pp. 2110-2117.
Evgeny Krestyannikov, et al. "Quantitatively Accurate Data Recovery from Attenuation-Corrected Sinogram Using Filtering of Sinusoidal Trajectory Signals", Conf. Rec. of IEEE Medical Imaging Conferences, Rome 2004, 5 pages.
Evgeny Krestyannikov, et al. "Noise Models for Sinusoidal Trajectories Composing Sinogram Data in Positron Emission Tomography"; Proceedings of the 6TH Nordic Signal Processing Symposium-Norsig 2004; Jun. 9-11, 2004; Espoo; Finland.
Francisco J. Caramelo, et al. "Image Reconstruction by Sinogram Decomposition into Sinusoidal Curves", Conf. Rec. of the 8TH Int. Meeting on Fully 3D Image Reconstruction in Radiology and Nuclear Medicine, Salt Lake City, Utah, USA, Jul. 2005, pp. 55-59.
B. Ohnesorge et al. "Efficient Correction for CT Image Artifacts Caused by Objects Extending Outside the Scan Field of View", Med. Phys. 27 (1), Jan. 2000, pp. 39-46.
J. Hsieh, et al. "A Novel Reconstruction Algorithm to Extend the CT Scan Field-of-View", Med. Phys. 31 (9), Sep. 2004, pp. 2385-2391.

* cited by examiner

*Primary Examiner*—Edward J Glick
*Assistant Examiner*—John M Corbett
(74) *Attorney, Agent, or Firm*—Oblon, Spivak, McClelland, Maier & Neustadt, P.C.

(57) ABSTRACT

A method for estimating projection data outside a field of view of a scanning device, including: obtaining measured projection data by scanning an object using the scanning device; selecting a projection angle and a fan angle outside a field of view of the scanning device; determining, based on the selected projection angle and fan angle, a plurality of sinogram curves, each sinogram curve corresponding to a different image point in the object; determining a contribution value for each of the sinogram curves based on the measured projection data; and calculating estimated expanded projection data for the selected projection angle and fan angle based on the determined contribution values.

25 Claims, 13 Drawing Sheets

METHOD, APPARATUS, AND COMPUTER PROGRAM PRODUCT FOR SINOGRAM COMPLETION

BACKGROUND OF THE INVENTION

Field of the Invention

The present invention relates generally to tomographic reconstruction. More specifically, the present invention relates to a new method for completing a truncated sinogram so as to extend the field of view of a scanning device by estimating unmeasured data based on interpolation within the measured data.

The present invention includes the use of various technologies referenced and described in the documents identified in the following LIST OF REFERENCES:

LIST OF REFERENCES

[1] Extension of the reconstruction field-of-view using sinogram decomposition, Alexander A. Zamyatin, Michael D. Silver, and Satoru Nakanishi, (submitted to the Proceedings SPIE Medical Imaging: Physics of Medical Imaging 6142 (April 2006), eds. M. J. Flynn/J. Hsieh, pp. 717-724, not printed);

[2] Extension of the reconstruction field of view and truncation correction using sinogram decomposition, Alexander A. Zamyatin, and Satoru Nakanishi, (submitted to Physics in Medicine and Biology Journal);

[3] Artifact reduction in truncated CT using Sinogram completion, R. Chityalya, K. R. Hoffman, S. Rudin, and D. R. Bednarek, filed concurrently with the present application (Proceedings SPIE Medical Imaging: Image Processing 5747 (April 2005), pp. 2110-2117);

[4] Quantitatively Accurate Data Recovery from Attenuation-Corrected Sinogram Using Filtering of Sinusoidal Trajectory Signals; Evgeny Krestyannikov, and Ulla Ruotsalainen, Conf. Rec. of IEEE Medical Imaging Conferences, Rome 2004;

[5] Noise Models for Sinusodial Trajectories Composing Sinogram Data in Positron Emission Tomography, Evgeny Krestyannikov, Antti Happonen, and Ulla Ruotsaliainen, Proceedings of the $6^{th}$ Noridc Signal Processing Symposium—NORSIG 2004, June 9-11, 2004, Espoo, Finland;

[6] Image Reconstruction by Sinogram Decomposition into Sinusodial Curves, Francisco J. Caramelo, Nuno C. Ferreira, Luis Fazendeiro, and Catarina Souto, Conf. Rec. of the $8^{th}$ Intl. Meeting on Fully 3D Image Reconstruction in Radiology and Nuclear Medicine, Salt Lake Cith, Utah, USA, July 2005, pp. 55-59;

[7] Efficient Correction for CT Image Artifacts Caused by Objects Extending Outside the Scan Field of View, B. Ohnesorge, T. Flohr, K. Schwartz, J. P. Heiken, and K. T. Bae, Med. Phys. 27 (1), pages 39-46 (2000); and

[8] A Novel Reconstruction Algorithm to Extend the CT Scan Field of View, J. Hsieh, E. Chao, J. Thibault, B. Grecowicz, A. Horst, S. McOlash, and T. J. Myers, Med. Phys. 31, pages 2385-2391 (2004).

The entire contents of each reference listed in the above LIST OF REFERENCES are incorporated herein by reference.

DISCUSSION OF THE BACKGROUND

A sinogram is obtained by stacking profile data from all projection angles. Sinogram truncation is a common problem in tomographic reconstruction. Sinogram truncation occurs when a scanned object or patient extends outside the field of view (FOV) of the scanning device. FIG. 1A shows an example of an object extending outside the scan FOV. As shown in FIG. 1A, a torso of a human subject is within the scan FOV, but the arms of the subject are within the extended FOV. FIG. 1B shows the resulting data truncation. Applications that suffer from sinogram truncation include PET/CT, radiation treatment planning, C-arm, and CT of large patients. For example, in PET/CT, the CT FOV is usually smaller than the PET FOV, which may lead to inaccurate correction.

In radiation treatment planning, a patient needs to be positioned a certain way on a flat bed and it is difficult to keep the patient within the FOV. Problems occur when a patient extends outside the FOV of the scanning device. For example, in radiation treatment planning, attenuation along each ray through a tumor is calculated. Since traditional reconstruction methods cannot reliably reconstruct images outside of the FOV, treatment planning becomes less accurate when the sinogram is calculated.

One way to avoid sinogram truncation is to redesign the scanning device to cover a larger FOV. However, this type of hardware solution is cost prohibitive, and results in longer data acquisition time. Another hardware solution is to shift the detector to one side so that the detector covers the extended FOV. However, this type of hardware solution is not possible with existing scanning devices, and may not be desired in future systems.

Most of the commercial CT scanners used today employ filtered-backprojection (FBP) algorithms that are very sensitive to truncated data in the projection data (i.e., the sinogram). At the place of truncation, there is a sharp drop in data values. Ramp convolution, used in FBP, results in an "explosion" of data values at the edge of truncation, which results in artifacts which appear near the truncated edge in the sinogram. Such artifacts propagate greatly degrade image quality.

SUMMARY OF THE INVENTION

Accordingly, to overcome the above-noted problems, the present invention seeks to provide a method, apparatus, and computer program product for estimating projection data outside a field of view of a scanning device.

According to a first aspect of the present invention, there is a method for estimating projection data outside a field of view of a scanning device, including: obtaining measured projection data by scanning an object using the scanning device; selecting a projection angle and a fan angle outside a field of view of the scanning device; determining, based on the selected projection angle and fan angle, a plurality of sinogram curves, each sinogram curve corresponding to a different image point in the object; determining a contribution value for each of the sinogram curves based on the measured projection data; and calculating estimated expanded projection data for the selected projection angle and fan angle based on the determined contribution values.

According to second aspect of the present invention, the step of determining a contribution value includes: interpolating the measured projection data along at least one of the plurality of sinogram curves.

According to a third aspect of the present invention, the step of calculating includes: calculating the estimated expanded projection data for the selected projection angle and fan angle based on a weighted sum of the contribution values for the plurality of sinogram curves.

According to a fourth aspect of the present invention, each contribution value is based on a minimum of the measured projection data on the corresponding sinogram curve.

According to a fifth aspect of the present invention, each contribution value is based on boundary values of the measured projection data on the corresponding sinogram curve.

According to a sixth aspect of the present invention, each contribution value is based on a minimum measured value of the measured projection data and on boundary values of the measured projection data on the corresponding sinogram curve.

According to a seventh aspect of the present invention, the method, further includes: storing a table including minimum values and boundary values of the measured projection data; and the step of calculating includes calculating the estimated expanded projection data using data included in the table.

According to an eighth aspect of the present invention, a computer readable medium storing instructions for execution on a computer system, which when executed by the computer system, causes the computer system to perform steps including: obtaining measured projection data by scanning an object using the scanning device; selecting a projection angle and a fan angle outside a field of view of the scanning device; determining, based on the selected projection angle and fan angle, a plurality of sinogram curves, each sinogram curve corresponding to a different image point in the object; determining a contribution value for each of the sinogram curves based on the measured projection data; and calculating estimated expanded projection data for the selected projection angle and fan angle based on the determined contribution values.

According to a ninth aspect of the present invention, a scanning apparatus, includes: a scanning device configured to obtain measured projection data by scanning an object; a selection unit configured to select a projection angle and a fan angle outside a field of view of the scanning device; and a processor configured to: determine, based on the selected projection angle and fan angle, a plurality of sinogram curves, each sinogram curve corresponding to a different image point in the object, determine a contribution value for each of the sinogram curves based on the measured projection data, and calculate estimated expanded projection data for the selected projection angle and fan angle based on the determined contribution values.

According to a tenth embodiment, the boundary values are based on a slope of the corresponding sinogram curve.

According to an eleventh embodiment, the table is a minimum value table, and a peak of the minimum value table is rounded off.

Additional objects and advantages of the invention will be set forth in the description which follows.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Initially, the variables and parameters used in this specification include

| | |
|---|---|
| FOV | Field-of-view; |
| $x = (x_1, x_2)$ | image point in the Cartesian coordinates; |
| $x = (r_x, \beta_x)$ | image point in polar coordinates; |
| $\mu(x)$ | attenuation function to be reconstructed; |
| R | radius of source trajectory; |
| $\Gamma$ | half of fan-angle aperture/opening; |
| $\gamma$ | variable fan angle (FA), $-\Gamma \leq \gamma \leq \Gamma$; |
| $\beta$ | projection (source) angle; |
| $y = (R \cos \gamma, R \sin \gamma)$ | equation of helical trajectory; |
| $r_\gamma$ | radius corresponding to $\gamma$, $r_\gamma = \arcsin(r_\gamma/R)$; |
| $g(\beta, \gamma)$ | fan beam data in form of sinogram; |
| $S(r_x, \beta_x)$ | sinogram curve, or S-curve; |
| sFOV | Scan field-of-view; |
| eFOV | Extended field-of-view; |
| $r_0$ | radius of the scan-FOV; |
| $r_{max}$ | radius of the extended FOV; |
| $\Gamma_0$ | FA of the scan-FOV; and |
| $\Gamma_{max}$ | FA of the extended FOV. |

Figure 2:
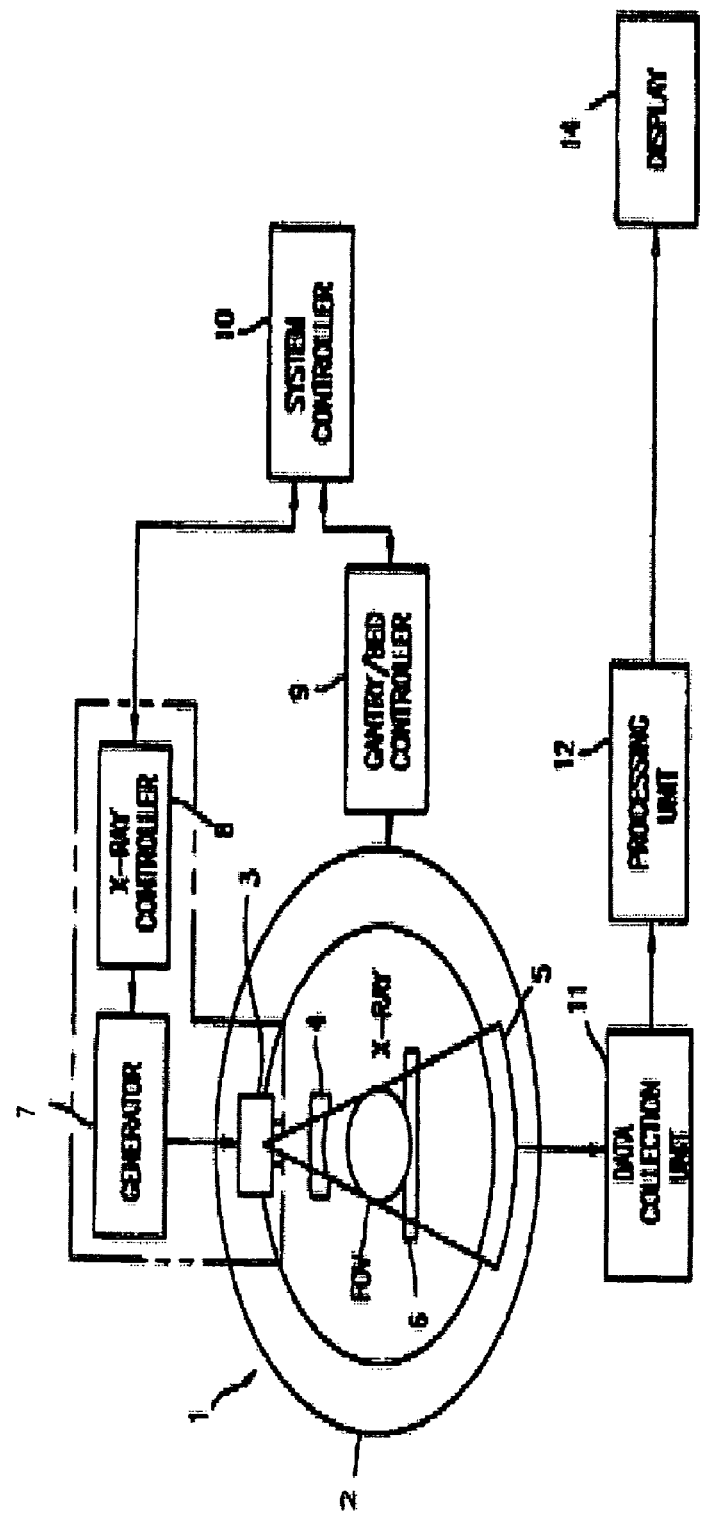
FIG. 2 shows an exemplary scanning device.

Referring now to the drawings, wherein like reference numerals designate identical or corresponding parts throughout the several views, FIG. 2 shows an x-ray computed-topographic imaging device that can be used to obtain data that is processed by methods of the present invention. However, the present invention may also be used with PET (positron emission tomography), SPECT (single photon emission tomography), and multi-modality applications, such as PET/CT and SPECT/CT.

The projection data measurement system constituted by gantry 1 accommodates an x-ray source 3 that generates a fan-beam of x-ray flux, and a two-dimensional array-type x-ray detector 5 consisting of a plurality of detector elements arranged in a two-dimensional fashion, i.e., a plurality of elements arranged in one dimension stacked in a plurality of rows. X-ray source 3 and two-dimensional array-type x-ray detector 5 are installed on a rotating ring 2 in facing opposite sides of a subject, who is laid on a sliding sheet of a bed or platform 6. Two-dimensional array-type x-ray detector 5 is mounted on rotating ring 2. Each detector element corresponds to one channel. X-rays from x-ray source 3 are directed onto the subject through an x-ray filter 4. X-rays that have passed through the subject are detected as an electrical signal by two-dimensional array type x-ray detector 5.

X-ray controller 8 supplies a trigger signal to high voltage generator 7. High voltage generator 7 applies high voltage to x-ray source 3 based on the timing with which the trigger signal is received. This causes x-rays to be emitted from x-ray source 3. Gantry/bed controller 9 synchronously controls the revolution of rotating ring 2 of gantry I and the sliding of the sliding sheet of bed 6. System controller 10 constitutes the control center of the entire system and controls x-ray controller 8 and gantry/bed controller 9 such that, as seen from the subject, x-ray source 3 executes so-called helical scanning, in which the X-ray source moves along a helical path. Specifically, rotating ring 2 is continuously rotated with fixed angular speed while the sliding plate is displaced with fixed speed, and x-rays are emitted continuously or intermittently at fixed angular intervals from x-ray source 3.

Furthermore, in alternative embodiments, x-ray source 3 and detector 2 may be stationary while the object being scanned is rotated.

The output signal of two-dimensional array type x-ray detector 5 is amplified by a data collection unit 11 for each channel and converted to a digital signal to produce projection data. The projection data may be in the form of a sinogram.

Figure 1A:
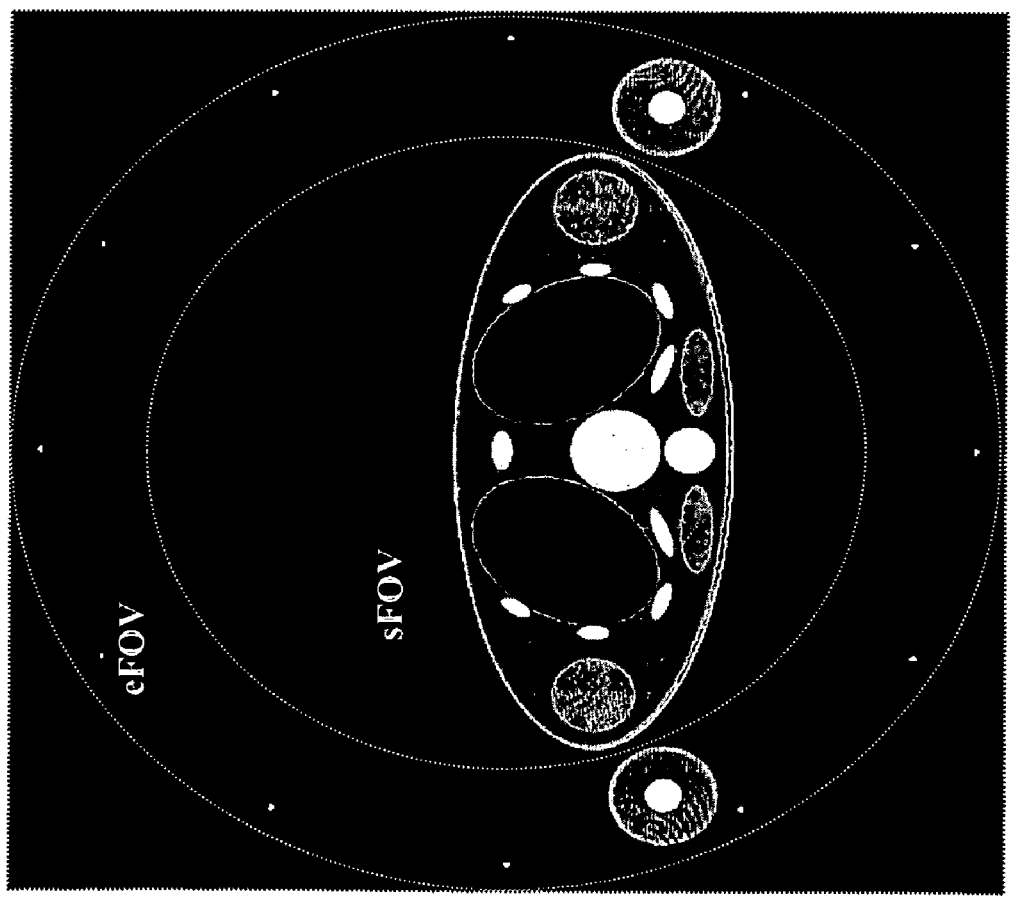
FIG. 1A shows an example of an object extending outside the scan FOV.
Figure 1B:
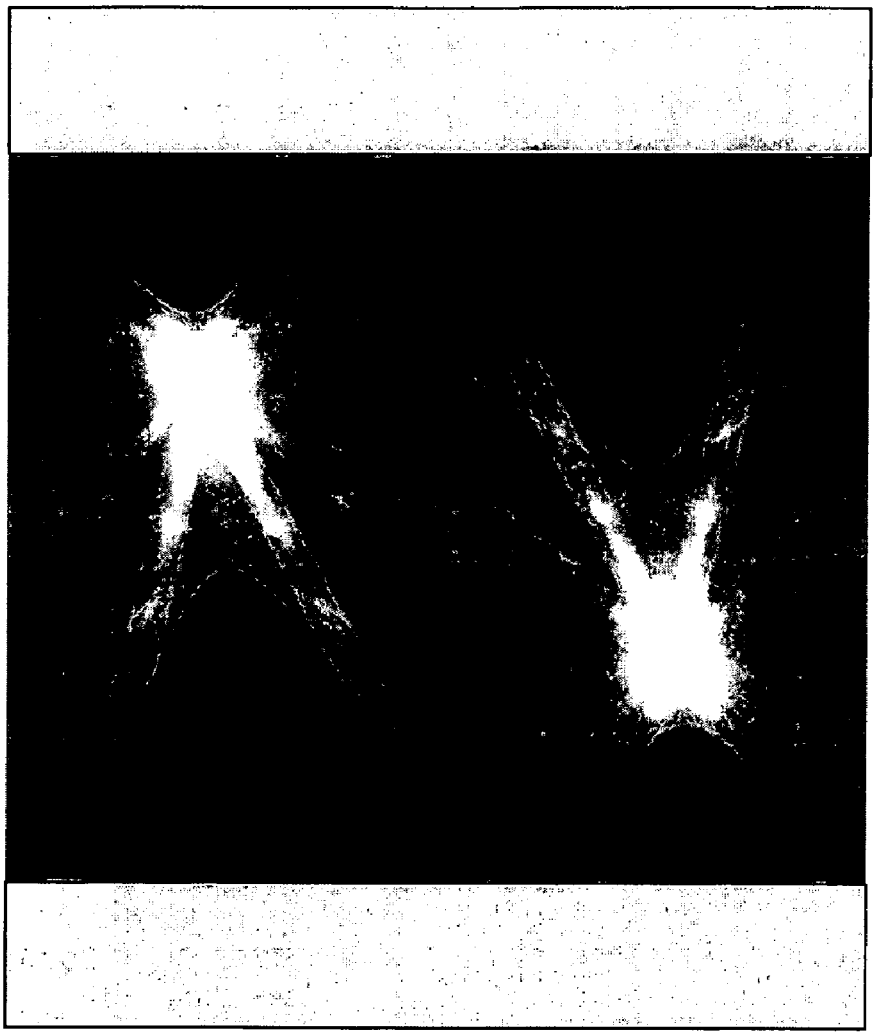
FIG. 1B shows the resulting data truncation from FIG. 1A.

FIG. 1B shows an exemplary sinogram generated by the above-noted device. This particular sinogram is truncated as indicated by the breaks or gaps in the sinusoidal curves. The truncated sinogram is missing data for a combination of fan angle $\gamma$ and projection angle $\beta$ that are outside the sFOV.

The projection data that is output from data collection unit 11 is fed to reconstruction processing unit 12. Reconstruction processing unit 12 uses the measured projection data (g, fan beam data in the form of a sinogram) to estimate the attenuation function for portions of the subject being scanned that extend outside the sFOV. Expanded projection data is generated by using the estimated attenuation function values. The algorithm used to reconstruct the attenuation function is discussed below.

In an additional embodiment, reconstruction processing unit 12 will find backprojection data reflecting the x-ray absorption in each voxel using expanded projection data, which is based on the reconstructed values of the attenuation function. Reconstruction processing unit 12 defines a plurality of voxels in this imaging region, and finds the backprojection data for each voxel.

The three-dimensional image data or tomographic image data compiled by using this backprojection data is sent to display device 14, where it is displayed visually as a three-dimensional image or tomographic image.

A helical scan generating a 3D image is only one embodiment of the present invention. Another embodiment is a circular scan producing only a 2D image.

In one embodiment of the present invention, un-measured attenuation data is estimated using measured projection data. The present invention is based on sinogram decomposition. There is a one-to-one correspondence between sinogram curves and image points. If some image point x is locate outside the sFOV, the majority of the s-curve for this image point x located outside of the sFOV can be extracted from the sinogram.

Contrary to the conventional extrapolation methods, an embodiment of the present invention utilizes interpolation along the sinogram curves to obtain an estimate of the un-measured attenuation data. The sinogram curve represents a path traced by projection of some object point as the X-ray source rotates around the isocenter. When an image point is placed far away from the isocenter outside the FOV, its s-curves cover a wide range of the fan angles. The inner part of the sinogram curve is always measured, providing a means to estimate the missing outer part. Using continuity of data along the s-curve, the truncated part of the s-curve can be interpolated between the measured parts, which allow a smooth completion of the s-curve.

Figure 3A:
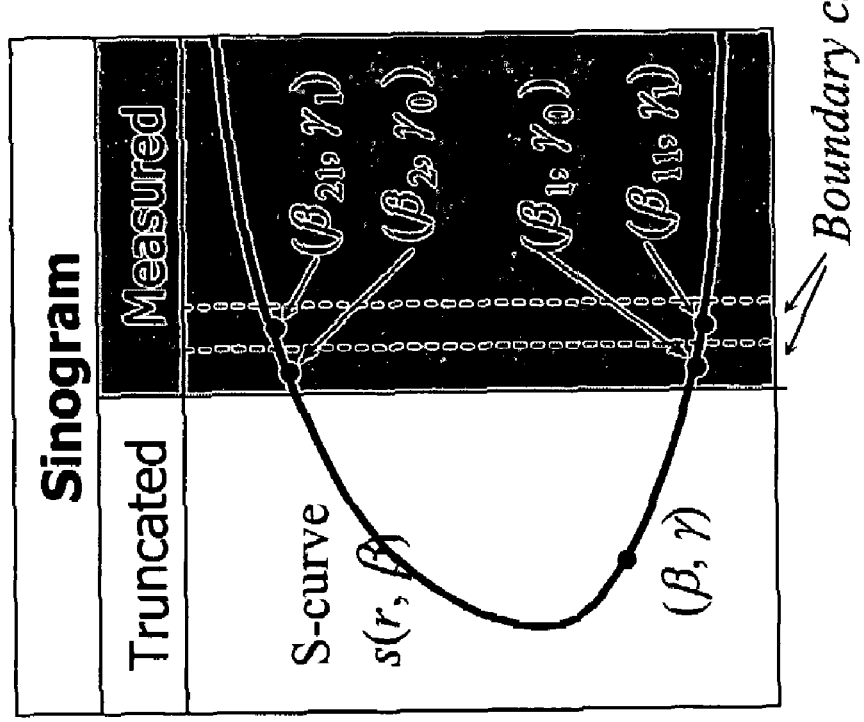
FIG. 3A shows the exemplary sinogram curve with interpolated data.

FIG. 3A shows how an s-curve for a point outside the sFOV is extracted from the sinogram by interpolation between measured data within the sinogram. For a point $(\beta, \gamma)$ that is outside the measured data, an s-curve through $(\beta, \gamma)$ can be created by interpolating between the partial s-curves in the measured data. The dashed line represents the measured data, and the completed sine curve (solid curved line) indicates the interpolated data. The interpolation will be repeated for each s-curve through $(\beta, \gamma)$. Further analysis needed to generate projection data at $(\beta, \gamma)$ is discussed below.

Figure 3B:
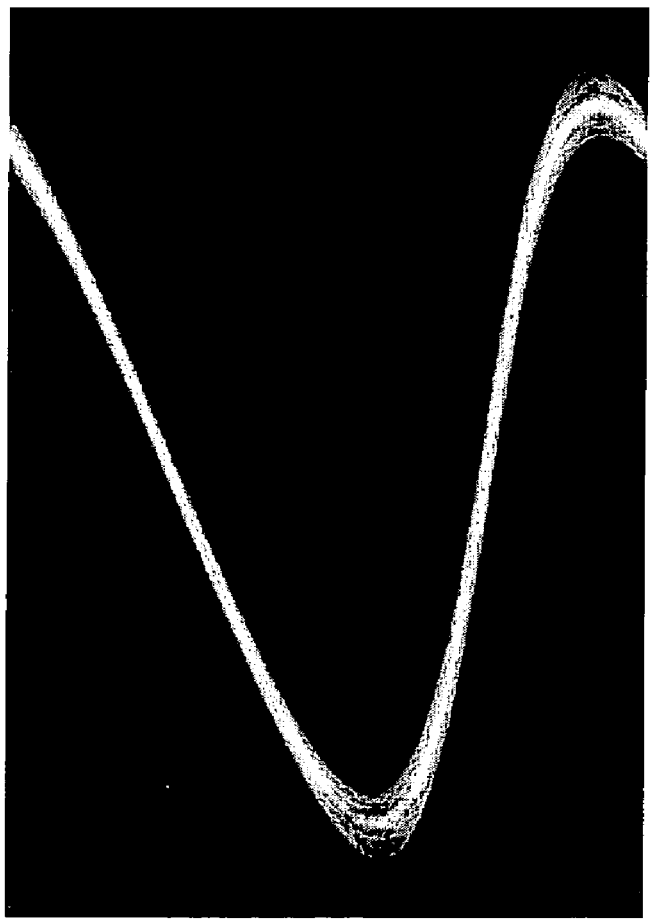
FIG. 3B shows an exemplary comparison between a truncated sinogram and a completed sinogram.

FIG. 3B shows an exemplary comparison between an original truncated sinogram and sinogram restored using an embodiment of the present invention.

Thus, one embodiment of the present invention involves moving from the center of the portion of the sinogram (non-truncated portion of the sinogram) outwards, to fill-in the truncated sinogram curves one by one.

The method of expanding the sFOV to the eFOV by completing the truncated sinogram will be derived for a fan beam CT device. However, as can be appreciated by persons of ordinary skill in the art, the present invention can be extended to circular cone beam, helical fan beam, and helical cone beam CT devices. Furthermore, as noted above, the device need not be limited to a CT device.

Projection data (i.e., a sinogram) of an object is obtained from a scanning device, as depicted in FIG. 2. Furthermore, in alternative embodiments, projection data may be generated in a first location, and can be transmitted to a second location for further analysis.

Figure 5:
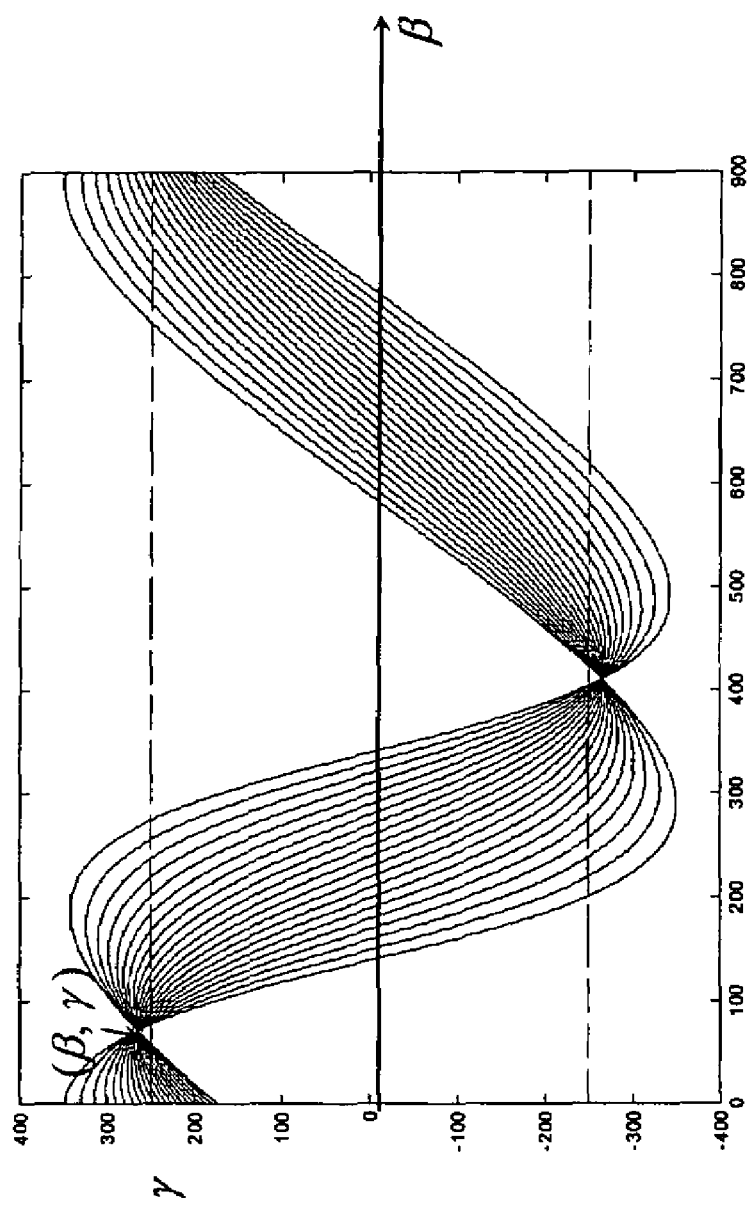
FIG. 5 shows a family of sinogram curves passing through a point in sinogram space corresponding to a point of unmeasured data.

One embodiment of the present invention estimates unmeasured attenuation data on a point by point basis. For the obtained sinogram, a given point (defined by a projection angle and a fan angle) is selected. FIGS. 3A and 5 show a point $(\beta, \gamma)$ that corresponds to unmeasured data.

Based on the selected point, defined by a selected projection angle and fan angle, a plurality of sinogram curves passing through the selected point are determined. A plurality of s-curves passing through a selected point $(\beta, \gamma)$ outside of the FOV is shown in FIG. 5. The portions of the s-curves between the two dashed lines correspond to measured portions of the s-curve (s knot). The portions of the s-curves outside of the dashed lines are unmeasured portions of the s-curves. The plurality of s-curves is determined by using the sinogram curve equation, which is derived below.

Figure 4:
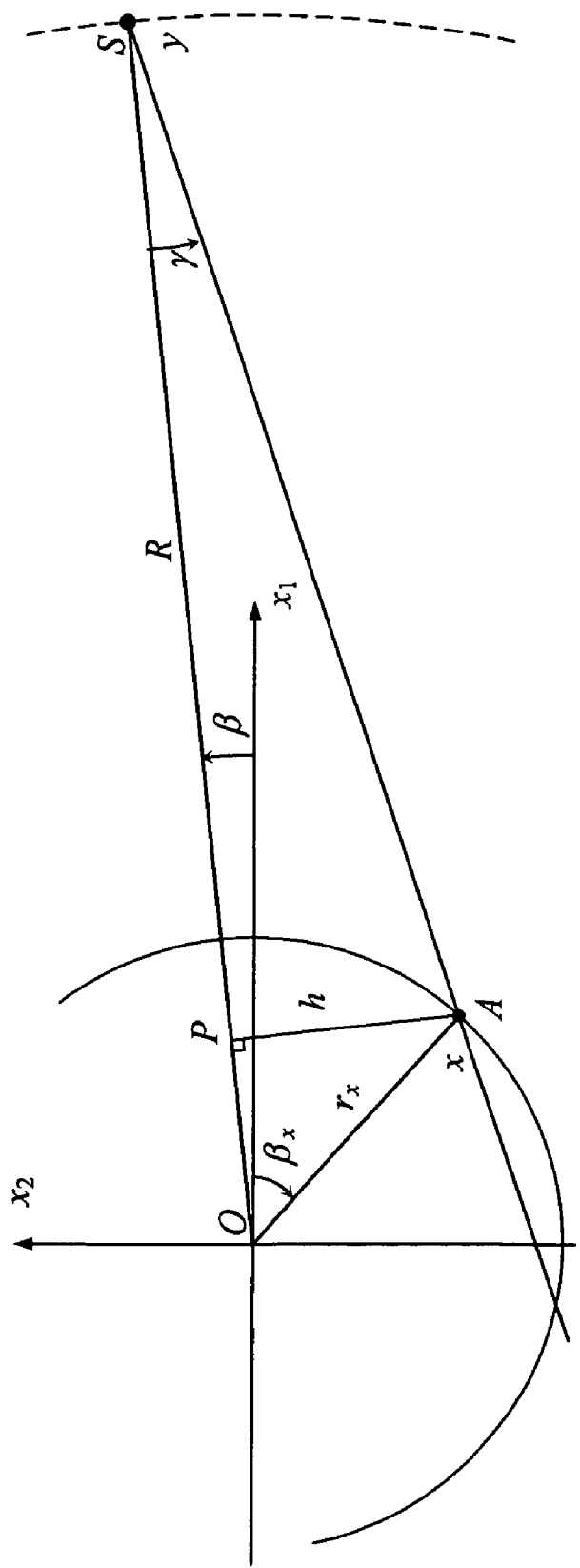
FIG. 4 shows a first exemplary arrangement of an X-ray source with respect to an object being scanned.

FIG. 4 shows of an exemplary arrangement of a CT scanning device. By using basic geometry, an equation defining a sinogram curve can be obtained. A sinogram curve is obtained by projecting a single image point x into a sinogram domain. In sinogram space, each image point is represented by a sinusoidal curve.

As shown in FIG. 4, image point x is given by its Cartesian coordinates $(x_1, x_2)$ or its polar coordinates $(r_x, \beta_x)$ The trajectory of the X-ray source (focal spot) S is given by $(R \cos \gamma, R \sin \gamma)$.

Using the geometry of the arrangement shown in FIG. 4, a conventional equation using Cartesian coordinates, a distance free equation (i.e., independent of R); and a polar coordinate equation can be derived that defines gamma. $\gamma$, in turn, can be used in defining a sinogram curve (or S-curve).

Below is the derivation of the sinogram equation:

$$\tan\gamma = \frac{PA}{PS}, \sin\gamma = \frac{PA}{AS}$$

Conventional Equation $$AS = |x-y| = \sqrt{(x_1 - R\cos\beta)^2 + (x_2 - R\sin\beta)^2} \quad (1)$$

$$PA = x \cdot (\cos\beta, \sin\beta)^\perp = x_1 \sin\beta - x_2 \cos\beta$$

$$\gamma = \arcsin\frac{x_1 \sin\beta - x_2 \cos\beta}{\sqrt{(x_1 - R\cos\beta)^2 + (x_2 - R\sin\beta)^2}}$$

Distance-Free Equation $$PS = OS - OP, OP = x \cdot (\cos\beta, \sin\beta) = x_1 \cos\beta + x_2 \sin\beta \quad (2)$$

$$\gamma = \arctan\frac{x_1 \sin\beta - x_2 \cos\beta}{R - (x_1 \cos\beta + x_2 \sin\beta)}$$

Equation in Polar Coordinates $$PA = OA \sin(\beta - \beta_x) = r_x \sin(\beta - \beta_x), \quad (3)$$

$$OP = r_x \cos(\beta - \beta_x) \Rightarrow PS = R - r_x \cos(\beta - \beta_x).$$

$$\gamma = \arctan\frac{r_x \sin(\beta - \beta_x)}{R - r_x \cos(\beta - \beta_x)}$$

The above equations (1), (2), and (3) can be used to define a sinogram curve. However, the equation in polar coordinate form will be used herein. A sinogram curve $S(r_x, \beta_x)$ is defined using a set notation:

$$S(r_x, \beta_x) = \left\{(\beta, \gamma) \mid 0 \le \beta < 2\pi, \gamma = \arctan\frac{r_x \sin(\beta - \beta_x)}{R - r_x \cos(\beta - \beta_x)}\right\} \quad (4)$$

Note that each s-curve is defined by $(r_x, \beta_x)$. Therefore these two parameters can be used to parameterize the whole family of sinogram curves. Furthermore, the family of s-curves thru the particular point $(\beta, \gamma)$ can be parameterized using only one parameter, $r_x$ or $\beta_x$.

Figure 6:
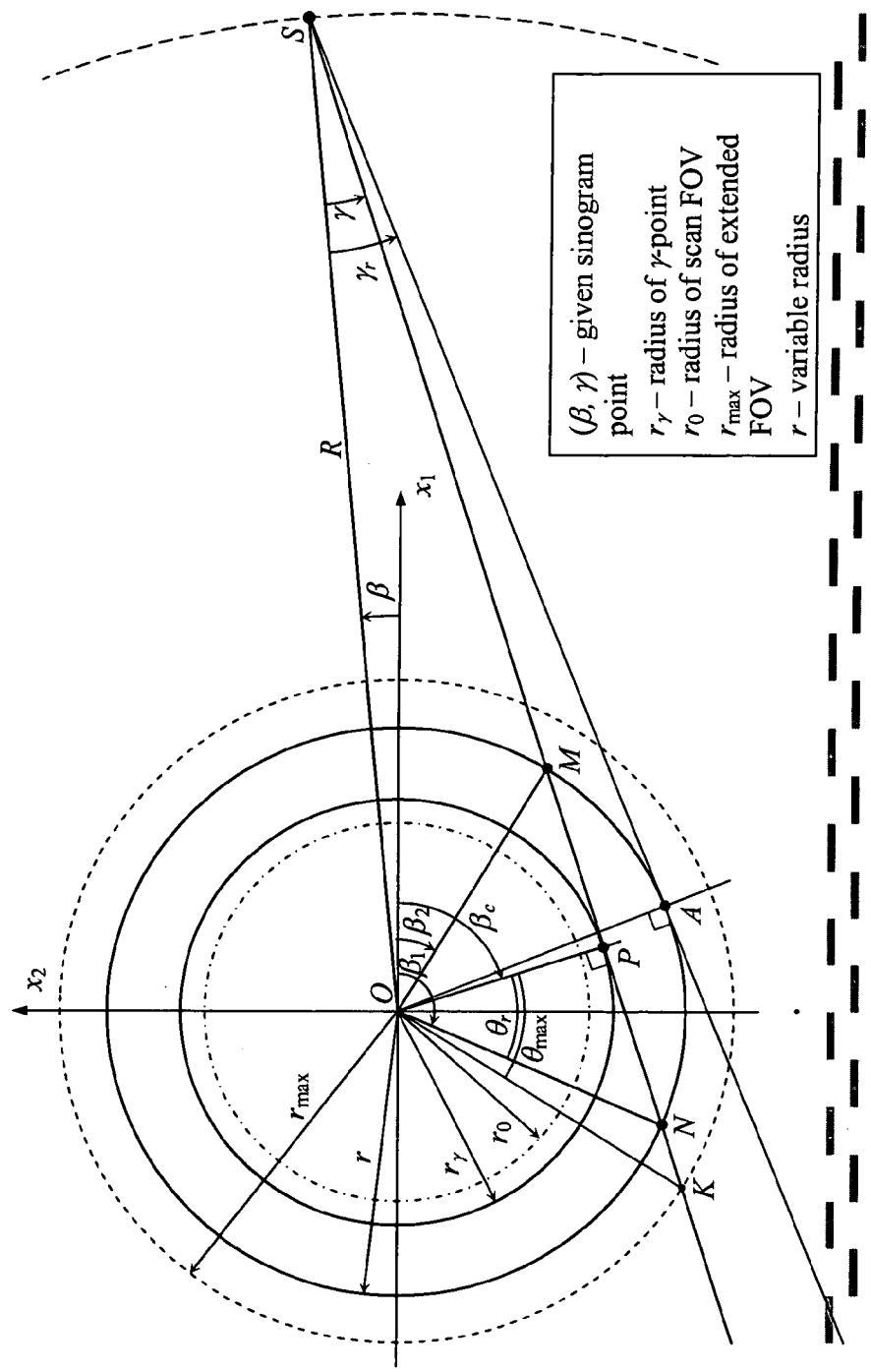
FIG. 6 shows a second exemplary arrangement of an X-ray source with respect to an object being scanned.

FIG. 6 shows a second arrangement of an X-ray source and object being scanned. As shown in FIG. 6, $r(\gamma)=R\sin\gamma$, which is the minimal radius for the family of curves. Therefore, the parameter r is bounded by $r_\gamma \le r \le r_{max}$, where $r_{max}$ is the radius of the extended FOV.

Many points on the scanned object (i.e., image points) contribute to the value of the point $(\beta, \gamma)$. FIG. 6 shows some of these points. $P(r_\gamma, \beta_c)$ is the point corresponding to the minimal radius, $r_\gamma$. $M(r, \beta_2)$ and $N(r, \beta_1)$ are two symmetrical (with respect to ray $\beta_c$) points, corresponding to an arbitrary radius $r \in [r_\gamma, r_{max}]$. Note that $\beta_1 = \beta_c + \theta_r$ and $\beta_2 = \beta_c - \theta_r$. $K(r_{max}, \beta_c - \theta_{max})$ is a point corresponding to the maximum radius, $r_{max}$. The symmetrical point, corresponding to $\beta_c + \theta_{max}$ is not shown.

As can be seen from FIG. 6, the following relationships can be established:

$$\beta_c = -\pi/2 + \beta + \gamma$$

$$\beta_1 = \beta_c + \theta_r$$

$$\beta_2 = \beta_c - \theta_r \quad (5)$$

$$\theta_r = \arccos(r_\gamma/r)$$

In the above discussion, the parameter r was made independent, and $\beta_x$ was dependent on $r_x$. However, to achieve a more uniform distribution in the discrete family of S-curves, it is better to make the parameter $\beta_x$ independent. Thus, if $\beta_x$ varies from $\beta_c - \theta_{max}$ to $\beta_c + \theta_{max}$, $\theta_{max} = \arccos(r_\gamma/r_{max})$, and the corresponding $r_x$ is:

$$r_x = \frac{R\sin\gamma}{\sin(\gamma + \beta - \beta_x)}, \quad (6)$$

which can be also rewritten as $$r_x = \frac{r_\gamma}{\cos(\beta_c - \beta_x)}. \quad (7)$$

Now, letting $\beta_x$ vary from $\beta_c - \theta_{max}$ to $\beta_c + \theta_{max}$ in equation (4), and choosing $r_x$ according to one of equations (6) or (7), one-parametric family of s-curves $S(r_x, \beta_x)$ that contain $(\beta, \gamma)$, as shown in FIG. 5, can be obtained. Therefore, to restore the projection data for point $(\beta, \gamma)$, outside of the sFOV, we need to use all the s-curves passing through point $(\beta, \gamma)$.

The given point $(\beta, \gamma)$ is recovered as the weighted sum of values from the s-curves through that given point $(\beta, \gamma)$, and will explained below.

Conventionally, the fan beam transform is given in Cartesian coordinates as:

$$g(\beta, \gamma) = \int_0^\infty \mu(y(\beta) + t\theta)dt, \quad (8)$$

where $\theta$ is the ray unit vector, $\theta = (-\cos(\beta+\gamma), \sin(\beta+\gamma))$. Thus, equation (8) can be re-written as:

$$g(\beta, \gamma) = \int_0^\infty \mu(R\cos\beta - t\cos(\beta+\gamma), \quad (9)$$

$$R\sin\beta - t\sin(\beta+\gamma))dt.$$

In polar coordinates, equation (8) becomes:

$$g(\beta, \gamma) = \int_{\beta_c - \theta_{max}}^{\beta_c + \theta_{max}} \mu(r_x, \beta_x) \left|\frac{dt}{d\beta_x}\right| d\beta_x. \quad (10)$$

It can be shown that $$\frac{dt}{d\beta_x} = \frac{r_x}{\cos(\beta_x - \beta_c)}.$$

Therefore we have $$g(\beta, \gamma) = \int_{\beta_c - \theta_{max}}^{\beta_c + \theta_{max}} \mu(r_x, \beta_x) \frac{r_x}{\cos(\beta_x - \beta_c)} \bigg|_{r_x = r_s(\beta_x, \beta, \gamma)} d\beta_x, \quad (11)$$

where $r_x(\beta_x, \beta, \gamma)$ is given by equation (6) and $\beta_c$ is given by equation (5).

$\mu(x)$ represents the attenuation function for some image point. As shown in equation (8), the attenuation function for the image points is used to construct the projection data $g(\beta, \gamma)$, or the sinogram. However, only data within the sFOV is available to create the sinogram, which results in a sinogram that is truncated.

When $\mu(x) = \mu(r_x, \beta_x)$ is unknown, an estimate of $\tilde{\mu}(r_x, \beta_x)$ is used. This estimate is obtained using values on the corresponding sinogram curve, $S(r_x, \beta_x)$. The truncated part of the s-curve can be interpolated between the measured parts of the s-curve (as shown in FIG. 3B), which allows smooth completion of the s-curve. There are several ways to obtain $\tilde{\mu}(r_x, \beta_x)$.

Approach 1. Use the minimum function:

$$\tilde{\mu}_{min}(r_x, \beta_x) = \min_{(\beta, \gamma) \in S_0(r_x, \beta_x)} g(\beta, \gamma), \quad (12)$$

where $S_0(r_x, \beta_x)$ represents the measured part of $S(r_x, \beta_x)$. In this approach, a minimum value along a sinogram curve $S(r_x, \beta_x)$ is found, and this value is assigned to $\tilde{\mu}(r_x, \beta_x)$. Also, values below noise level can be thresholded out, which allows image points with no attenuation to be ruled out. This approach has an advantage that it accurately restores even remote sinogram points from small parts or objects. Its disadvantage is that it does not match the sinogram at the boundary.

Approach 2. Use boundary values of the measured sinogram that belong to $S(r_x, \beta_x)$ The boundary values correspond to $r = r_0$, and the $\beta$-coordinates are given by:

$$\beta_1 = \pi/2 + \beta_c - \gamma_0 + \theta_r \quad (13)$$
$$\beta_2 = \pi/2 + \beta_c - \gamma_0 - \theta_r$$
$$\theta_r = \arccos \frac{r_0}{r_x}$$
$$v_1 = g(\beta_1, \gamma_0)$$
$$v_2 = g(\beta_2, \gamma_0)$$
$$g_{bs}(\beta, \gamma) = \frac{\beta_2 - \beta}{\beta_2 - \beta_1} v_1 + \frac{\beta - \beta_1}{\beta_2 - \beta_1} v_2$$

(Note: $\beta_1, \beta_2, \theta_r$ are temporary variables and are not the same as in equation (5)).

Figure 3B:
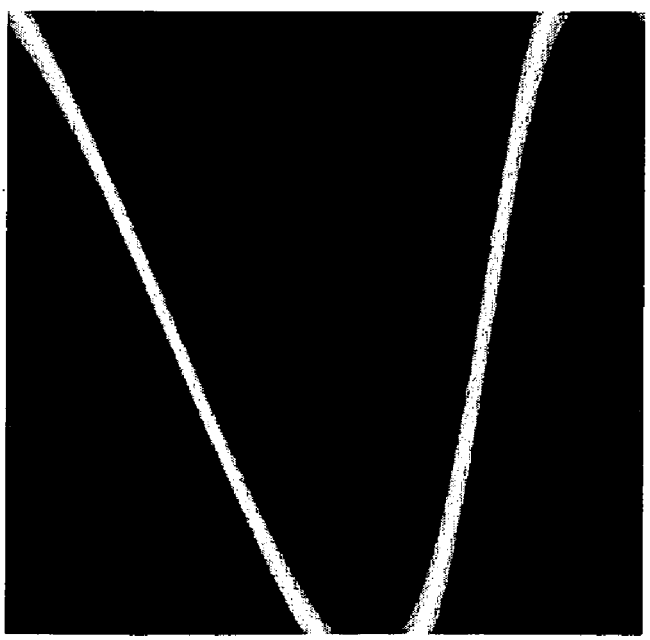

Approach 2 using Slopes (see FIG. 3):

$$\gamma_{01} = \gamma_0 - d\gamma \quad (14)$$
$$r_{01} = R \sin \gamma_{01}$$
$$\beta_{11} = \pi/2 + \beta_c - \gamma_{01} + \theta_r$$
$$\beta_{21} = \pi/2 + \beta_c - \gamma_{01} - \theta_r$$

$$\theta_r = \arccos \frac{r_{01}}{r} \quad (15)$$

$$v_{11} = g(\beta_{11}, \gamma_{01}) \quad (16)$$
$$v_{21} = g(\beta_{21}, \gamma_{01})$$
$$Slope1 = v_1 - v_{11}$$
$$Slope2 = v_2 - v_{21}$$

$$g_{bs}(\beta, \gamma) = (v1 + Slope1 \cdot (\gamma - \gamma_0)) \frac{\beta - \beta_2}{\beta_1 - \beta_2} + \quad (17)$$
$$(v2 + Slope2 \cdot (\gamma - \gamma_0)) \frac{\beta_1 - \beta}{\beta_1 - \beta_2}$$

The final boundary estimate $g_b(\beta, \gamma)$ is obtained by averaging $g_{bs}(\beta, \gamma)$ corresponding to all s-curves through $(\beta, \gamma)$. The advantage of approach 2 is that it very smoothly extends the sinogram so that truncation artifacts on the edge of the boundary are reduced to a minimum. The disadvantage of approach 2 is that it becomes inaccurate deep in the truncated zone (i.e., for large values of $\gamma$).

Approach 3. Use a combination of approaches 1 and 2.

In another embodiment of the present invention, feathering is used such that Approach 2 is used near the edge of truncation (i.e., small value of $\gamma$), and Approach 1 is used further away from the edge of truncation (i.e., large values of $\gamma$). Accordingly, the following estimate for the missing attenuation value is given by:

$$\tilde{\mu}(r_x, \beta_x) = w_r(r_x)\tilde{\mu}_{min}(r_x, \beta_x) + (1 - w_r)\tilde{\mu}_{bnd}(r_x, \beta_x), \quad (18)$$

Minimum Value Table

Figure 8A:
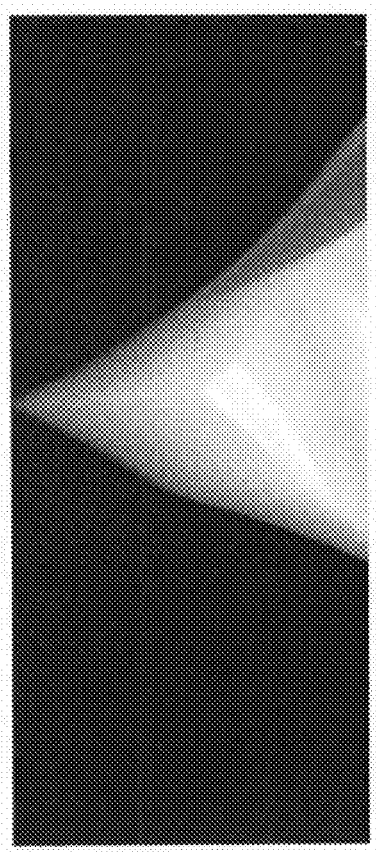
FIG. 8A shows a minimum value table from truncated data.
Figure 8B:
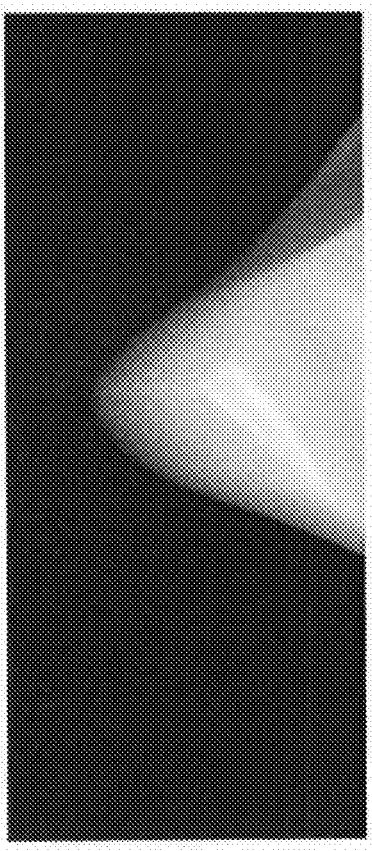
FIG. 8B shows a corrected minimum value table.

A minimum value table (MVT) may be used to improve the efficiency of the present invention. An exemplary minimum value table is shown in FIGS. 8A and 8B. FIG. 8A shows an MVT obtained from the truncated data. FIG. 8B shows a corrected MVT. In one embodiment of the present invention, the minimum value table includes pre-calculated values of $\tilde{\mu}_{min}(r_x, \beta_x)$ and $[v_1, v_2](r_x, \beta_x)$ In yet another embodiment, the minimum value table, or a different table, may store Weighted Minimum Value Table (WMVT) $\tilde{\mu}_{min}(r_x, \beta_x)$ and Weighted Boundary Values Table (WBVT) $[v_1, v_2](r_x, \beta_x)$.

Thus, in an efficient implementation of the present invention, rather than calculating $\tilde{\mu}_{min}(r_x, \beta_x)$ and $[v_1, v_2](r_x, \beta_x)$, these values can be looked up in the minimum value table for each $(r_x, \beta_x)$.

MVT Post-Processing

The obtained MVT needs to be modified. This is necessary because the data is truncated, and therefore MVT becomes distorted. In particular, truncation results in additional peaks in the obtained MVT that are directed away from the center. Such peaks, if not corrected, result in blurry edges on the far side of the object. There are many methods that can be employed to correct peaks; it is a rather standard problem in signal processing. FIGS. 8A and 8b illustrate how the peaks need to be corrected.

Weighting

Weighting is required when the reconstructed object does not consist of disjoint single points. Thus, in practice, weighting is always needed. The weighting needs to account for two effects: (1) the missing value g(β, γ) is restored from N sinogram curves, where N depends on many things in general; and (2) sampling pitch Δβ$_x$ (sampling of the family of S-curves). g(β, γ) should not depend on sampling size. Therefore, the applied weighting should normalize the obtained value to the sampling pitch.

Figure 7:
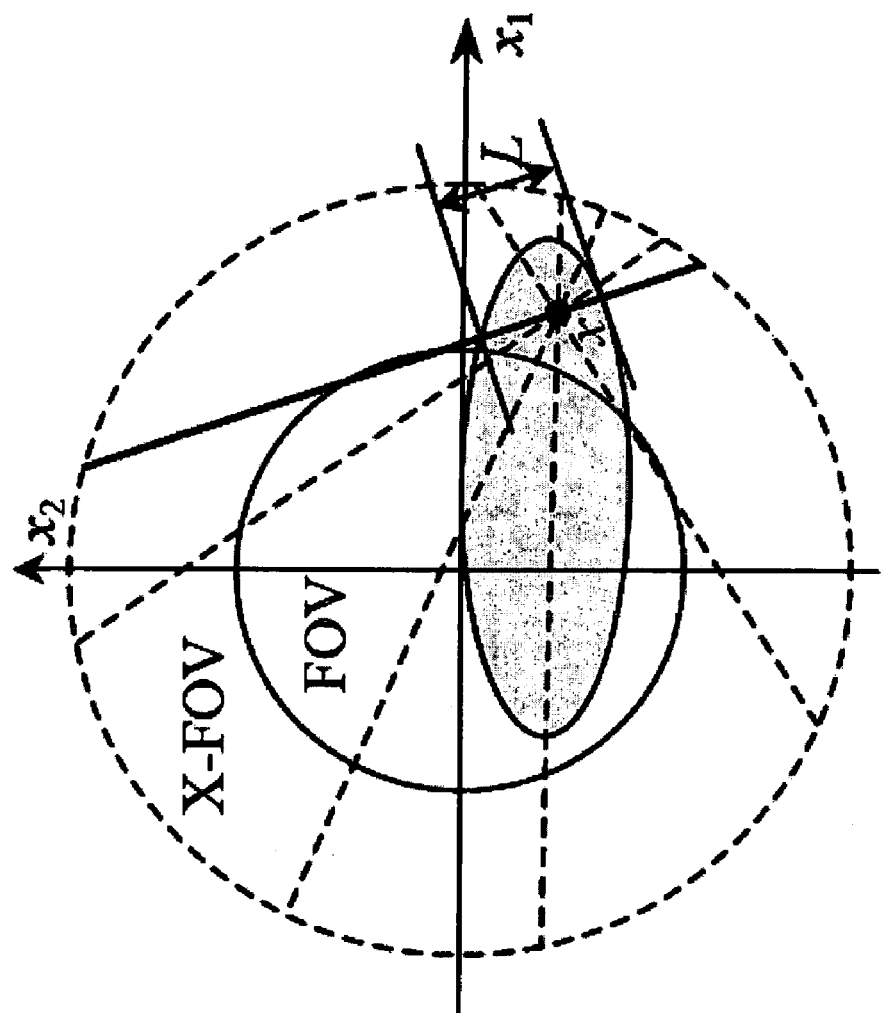
FIG. 7 shows a family of measured line integrals through a given image point.

Since the scanned object has width, contrary to a single point, the obtained minimum estimate $\tilde{\mu}_{min}(r_x, \beta_x)$ represents the integral thru the thinnest part of the object, as seen within the sFOV. By assuming that the scanned object has uniform attenuation, the weighting becomes simplified in that $\tilde{\mu}_{min}(r_x, \beta_x)$ needs to be normalized by the length L of this shortest measured path: $\tilde{\mu}(r_x, \beta_x) = \tilde{\mu}_{min}(r_x, \beta_x)/L$ FIG. 7 shows a family of measured line integrals through a given image point (β, γ). The solid line represents $\tilde{\mu}_{min}(r_x, \beta_x)$, and L is shown as the shortest measured path through the scanned object.

Figures 9A, 9B, 9C:
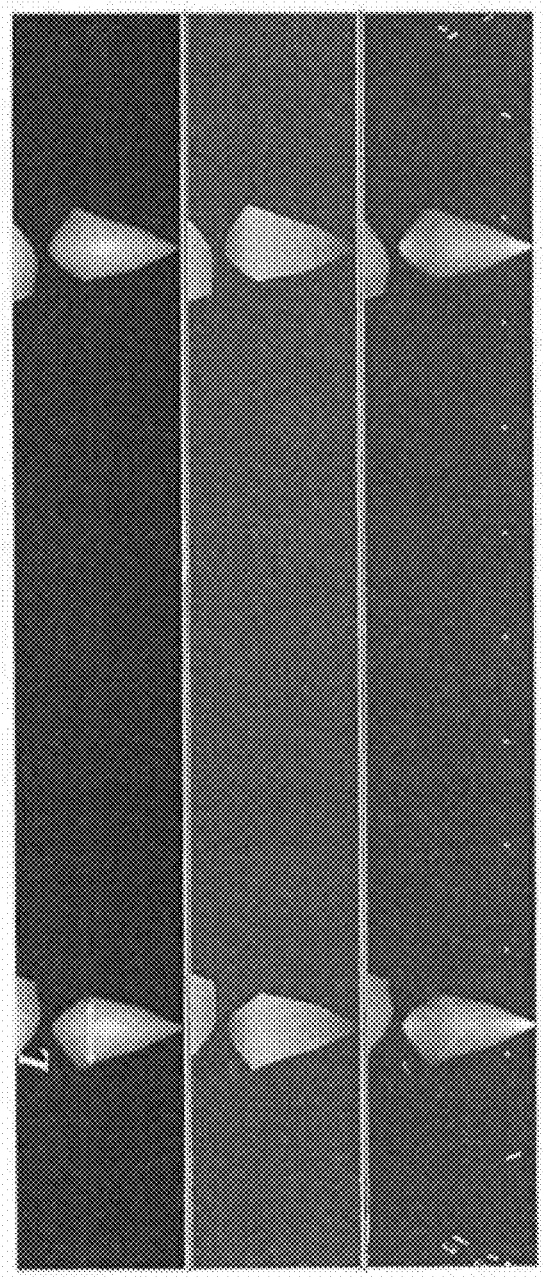
FIG. 9A shows a minimum value table indicating the length of the shortest measured path.
FIG. 9B shows a L-weighting table.
FIG. 9C shows a weighted minimum value table.

Note that L is not known and needs to be estimated too. L can be estimated by using the Minimum Value Table (MVT) $\tilde{\mu}_{min}(r_x, \beta_x)$. FIG. 9A shows how L can be estimated from the MVT. FIG. 9B shows an L weighting table. FIG. 9C shows a weighted MVT. L can be estimated as:

$$L = \frac{r_x \sin \Delta \beta_x}{\cos(\beta_x - \beta_c)} \quad (19)$$

where Δβ$_x$ is the angular span of L. So Eq. (20) takes the form of:

$$g(\beta, \gamma) = \int_{\beta_c - \theta_{max}}^{\beta_c + \theta_{max}} \tilde{\mu}_{min}(r_x, \beta_x) \frac{1}{\sin \Delta \beta_x} d\beta_x. \quad (20)$$

Or $$g(\beta, \gamma) = \int_{\beta_c - \theta_{max}}^{\beta_c + \theta_{max}} \tilde{\mu}_{min}(r_x, \beta_x) w_{\Delta \beta_x} d\beta_x. \quad (21)$$

Where $w_{\Delta \phi}$ is the minimum value weight and can be estimated by $$w_{\Delta \phi} = \sin(\text{count} \cdot ds/2)/2 \cdot \text{min\_weight\_factor}$$

where count is the number of non-zero points on the ray (or, equivalently, number of sinogram curves through this data pixel), and the min_weight_factor is taken into account to match the analytic expressions with the raw data. Experimentally, min_weight_factor=0.0085.

Exemplary Implementation

The following describes an exemplary implementation of one embodiment of the present invention. The input data is $g_0(\beta, \gamma)$, where $0 \leq \beta < 2\pi$, and $-\Gamma_0 \leq \gamma \leq \Gamma_0$. This sinogram will be truncated. The output data is a completed sinogram (i.e., expanded by estimating unmeasured data) g(β, γ), where $0 \leq \beta < 2\pi$, and $-\Gamma_{max} \leq \gamma \leq \Gamma_{max}$.

The outer-most loop, the eFOV as shown in FIG. 6, takes on all truncated values of (β, γ). For simplicity, let us consider only one side, $\Gamma_0 < \gamma \leq \Gamma_{max}$. The other side ($-\Gamma_{max} \leq \gamma < -\Gamma_0$) is processed similarly.

Inside the outer-loop, the sinogram point (β, γ) is fixed. The family of sinogram curves S ($r_x, \beta_x$) thru this point is found. As discussed previously, $\beta_x$ is an independent parameter such that $\beta_c - \theta_{max} \leq \beta_x \leq \beta_c + \theta_{max}$, and $r_x$ is found as a function of $\beta_x$, β, and γ.

Therefore an intermediate loop (loop with radius r in FIG. 6) takes on values of $\beta_x$ between $\beta_c - \theta_{max}$ and $\beta_c + \theta_{max}$ (see equation (5)), and the corresponding $r_x$ is found using equations (6) or (7).

Now, once the pair ($r_x, \beta_x$) is also fixed, its contribution, i.e. some value $\tilde{\mu}(r_x, \beta_x)$ is found. In this example, the minimum value technique will be used as it will limit the range of S-functions. We will follow the curve S ($r_x, \beta_x$) to find $\tilde{\mu}_{min}(r_x, \beta_x)$ This is the inner-most loop (sFOV), where: β' changes from 0 to 2π, and find γ' as a function of β', $\beta_x$, and $r_x$ using equation (3) (prime "'" is used to differ from the outer-most (β, γ)). The outcome of the inner-most loop is $\tilde{\mu}_{min}(r_x, \beta_x)$.

The speed of processing can be increased by exiting the inner-most loop if the minimum value falls below the noise threshold (in analytic noiseless simulations, exit if it equals to zero). If $\tilde{\mu}_{min}(r_x, \beta_x) = 0$, we can definitely say that $\mu(r_x, \beta_x) = 0$, which is by itself a useful result.

At the end of the intermediate loop we need to calculate $\tilde{\mu}_{bnd}(r_x, \beta_x)$ (boundary), $\tilde{\mu}(r_x, \beta_x)$ and accumulate all available values (for each s-curve through point (β, γ)) as some temporary variable.

At the end of the outer-most loop, the accumulating temporary variable assigned to the missing data g(β, γ). All temporary variables are zeroed out here or whenever necessary.

In another implementation of the present invention, minimum and boundary values are pre-calculated, thus avoiding the inner-most loop. This more efficient implementation can be characterized as:

Pre-Calculate:
Weighted Minimum Value Table (WMVT) $\tilde{\mu}_{min}(r_x, \beta_x)$ and Boundary Values and Slope Tables (WBVT), $BVT_{left}(r_x, \beta_x)$, $SIT_{right}(r_x, \beta_x)$, $SIT_{left}(r_x, \beta_x)$; and Process Data:
Outer loop: for truncated (β, γ).
Inner loop: for S-curves S($r_x, \beta_x$).

(These two loops are the same as Outer-most and Intermediate loops as previously described, and further description is omitted).

Figure 10:
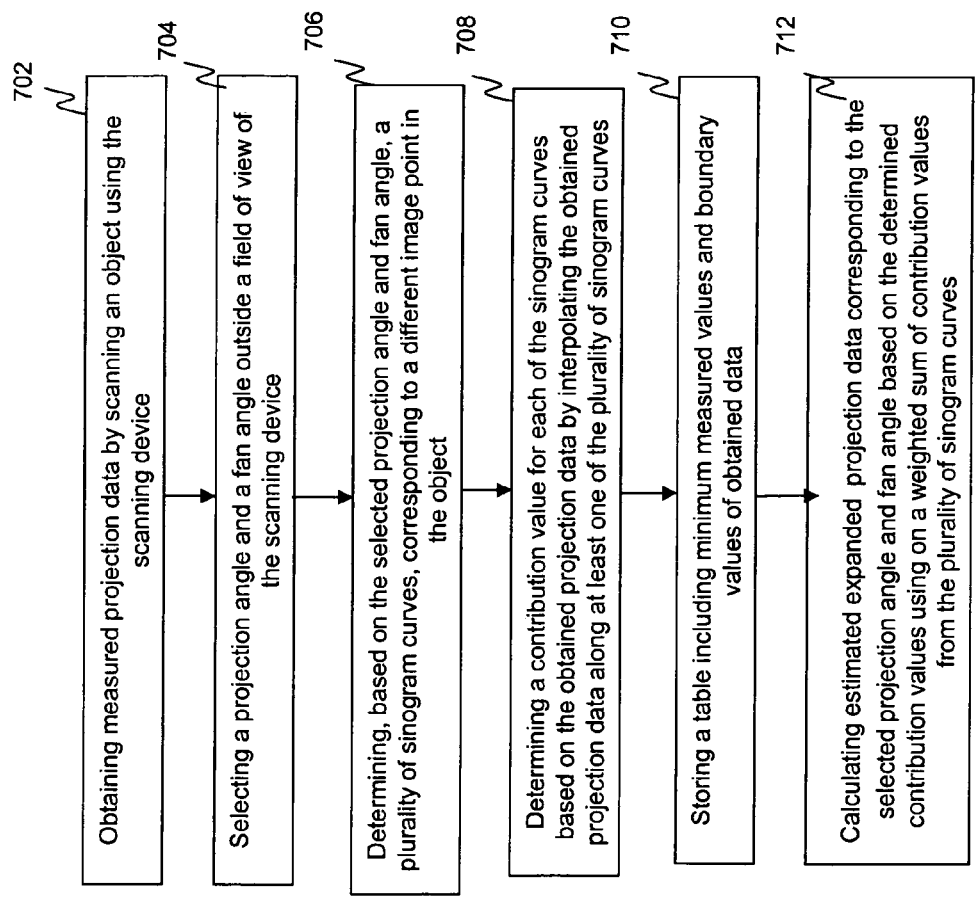
FIG. 10 shows an exemplary method for practicing an embodiment of the present invention.

FIG. 10 illustrates an exemplary method for implementing the present invention. In step 702, projection data is obtained using a scanning device. In step 704, a projection angle and a fan angle outside of the sFOV is selected. In step 706, based on the projection angle and fan angle selected in step 704, a plurality of sinogram curves, corresponding to different image points, are determined. The plurality of sinogram curves pass through the point selected in step 704. In step 708, a contribution value for each of the plurality of curves based on the measured data is determined by interpolating within the measured data along at least one of the plurality of curves. In step 710, a table is stored that includes minimum valued and boundary values of measured data. In step 712, projection data corresponding to the selected data and fan angles selected in step 704 is calculated based on the determined contribution values based on a weighted sum of contributions from the plurality of curves.

Figure 11:
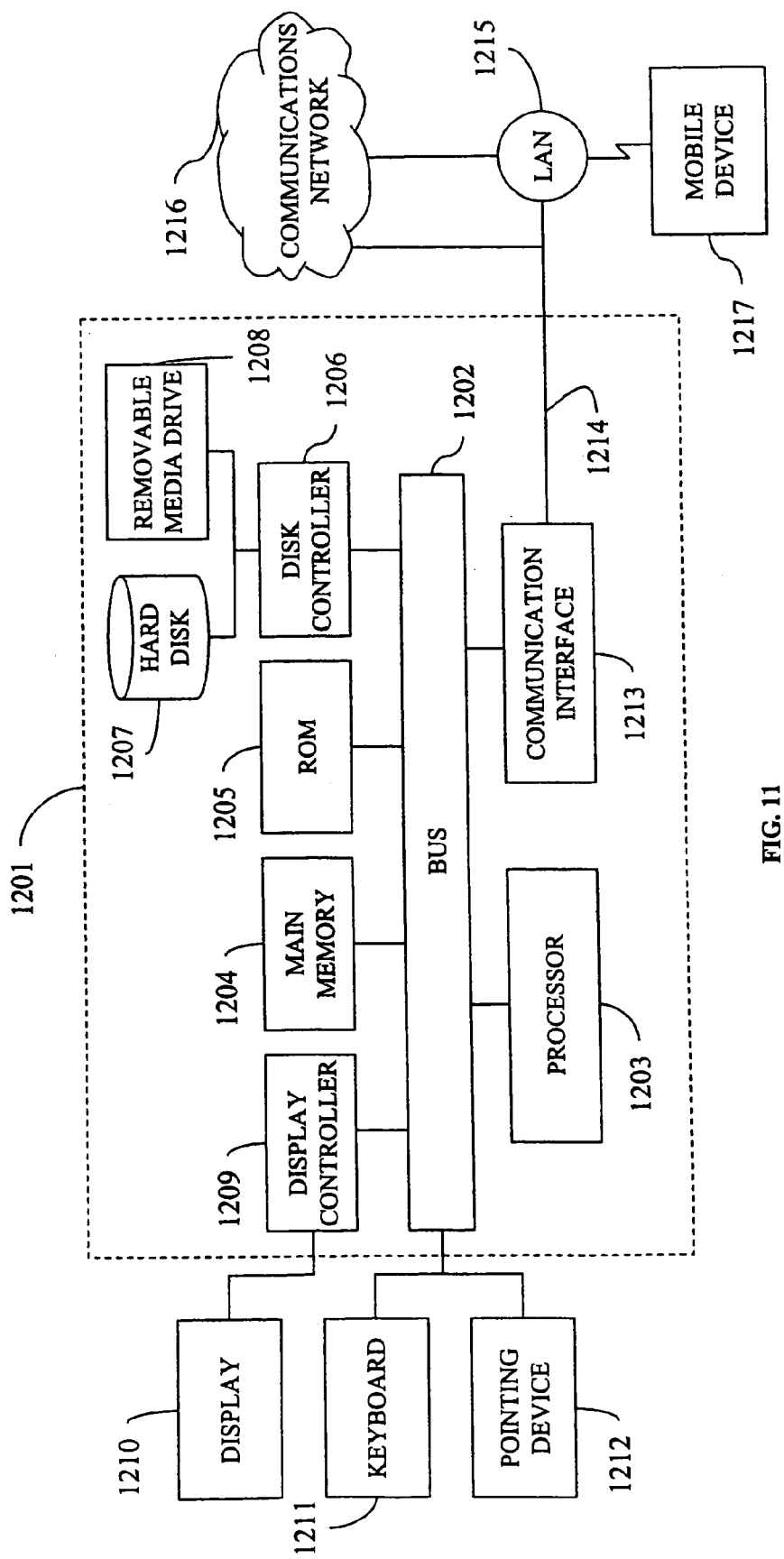
FIG. 11 is a block diagram of a computer system upon which an embodiment of the present invention may be implemented.

FIG. 11 illustrates a computer system 1201 upon which an embodiment of the present invention may be implemented. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable ROM (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, such as a cathode ray tube (CRT), for displaying information to a computer user. The computer system includes input devices, such as a keyboard 1211 and a pointing device 1212, for interacting with a computer user and providing information to the processor 1203. The pointing device 1212, for example, may be a mouse, a trackball, or a pointing stick for communicating direction information and command selections to the processor 1203 and for controlling cursor movement on the display 1210. In addition, a printer may provide printed listings of data stored and/or generated by the computer system 1201.

The computer system 1201 performs a portion or all of the processing steps of the invention in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, BEPROM, flash EPROM), DRAM, SRAM, SDRAM, or any other magnetic medium, compact discs (e.g., CD-ROM), or any other optical medium, punch cards, paper tape, or other physical medium with patterns of holes.

Stored on any one or on a combination of computer readable media, the present invention includes software for controlling the computer system 1201, for driving a device or devices for implementing the invention, and for enabling the computer system 1201 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices.

For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214 and the communication interface 1213. Moreover, the network link 1214 may provide a connection through a LAN 1215 to a mobile device 1217 such as a personal digital assistant (PDA) laptop computer, or cellular telephone.

All embodiments of the present invention may conveniently be implemented using a conventional general purpose computer or micro-processor programmed according to the teachings of the present invention, as will be apparent to those skilled in the computer art. Appropriate software may readily be prepared by programmers of ordinary skill based on the teachings of the present disclosure, as will be apparent to those skilled in the software art. In particular, the computer housing may house a motherboard that contains a CPU, memory, and other optional special purpose logic devices (e.g., ASICS) or configurable logic devices (e.g., GAL and reprogrammable FPGA). The computer also includes plural input devices, (e.g., keyboard and mouse), and a display card for controlling a monitor. Additionally, the computer may include a floppy disk drive; other removable media devices (e.g. compact disc, tape, and removable magneto-optical media); and a hard disk or other fixed high density media drives, connected using an appropriate device bus (e.g., a SCSI bus, an Enhanced IDE bus, or an Ultra DMA bus). The computer may also include a compact disc reader, a compact disc reader/writer unit, or a compact disc jukebox, which may be connected to the same device bus or to another device bus.

Stored on any one or on a combination of the above-noted or any other computer readable media, the present invention includes software for controlling both the hardware of the computer and for enabling the computer to interact with a human user. Such software may include, but is not limited to, device drivers, operating systems and user applications, such as development tools. Computer program products of the present invention include any computer readable medium which stores computer program instructions (e.g., computer code devices) which when executed by a computer causes the computer to perform the method of the present invention. The computer code devices of the present invention may be any interpretable or executable code mechanism, including but not limited to, scripts, interpreters, dynamic link libraries, Java classes, and complete executable programs. Moreover, parts of the processing of the present invention may be distributed (e.g., between (1) multiple CPUs or (2) at least one CPU and at least one configurable logic device) for better performance, reliability, and/or cost. For example, an outline or image may be selected on a first computer and sent to a second computer for remote diagnosis.

The invention may also be implemented by the preparation of application specific integrated circuits or by interconnecting an appropriate network of conventional component circuits, as will be readily apparent to those skilled in the art.

Furthermore, the source of image data to the present invention may be any appropriate image acquisition device such as an X-ray machine or CT apparatus. The acquired data may be digitized if not already in digital form.

Numerous modifications and variations of the present invention are possible in light of the above teachings. It is therefore to be understood that within the scope of the appended claims, the invention may be practiced otherwise than as specifically described herein.

The invention claimed is:

1. A method for estimating projection data outside a field of view of a scanning device, comprising:
    obtaining projection data by scanning an object using the scanning device;
    selecting a projection angle and a fan angle outside a field of view of the scanning device;
    determining, based on the selected projection angle and fan angle, a plurality of sinogram curves, each sinogram curve corresponding to a different image point in the object;
    determining a contribution value for each of the sinogram curves based on the obtained projection data;
    calculating estimated projection data for the selected projection angle and fan angle based on the determined contribution values; and
    storing the estimated projection data,
    wherein the step of determining the contribution value includes interpolating the obtained projection data along at least one of the plurality of sinogram curves.

2. The method of claim 1, wherein the step of calculating comprises:
    calculating the estimated projection data for the selected projection angle and fan angle based on a weighted sum of the contribution values for the plurality of sinogram curves.

3. The method of claim 1, wherein each contribution value is based on a minimum value of the obtained projection data on the corresponding sinogram curve.

4. The method of claim 1, wherein each contribution value is based on boundary values of the obtained projection data on the corresponding sinogram curve.

5. The method of claim 1, wherein each contribution value is based on a minimum value of the obtained projection data on the corresponding sinogram curve and on boundary values of the obtained projection data on the corresponding sinogram curve.

6. The method of claim 1, further comprising:
    storing a table including minimum values and boundary values of the obtained projection data; and
    said step of calculating includes calculating the estimated projection data using data included in the table.

7. The method of claim 4, wherein the boundary values are based on a slope of the corresponding sinogram curve.

8. The method of claim 6, wherein the table is a minimum value table, and a peak of the minimum value table is rounded off.

9. An apparatus for estimating projection data outside a field of view of a scanning device, comprising:
    means for obtaining projection data by scanning an object using the scanning device;
    means for selecting a projection angle and a fan angle outside a field of view of the scanning device;
    means for determining, based on the selected projection angle and fan angle, a plurality of sinogram curves, each sinogram curve corresponding to a different image point in the object;
    means for determining a contribution value for each of the sinogram curves based on the obtained projection data; and
    means for calculating estimated projection data for the selected projection angle and fan angle based on the determined contribution values,
    wherein the means for determining the contribution value includes means for interpolating the obtained projection data along at least one of the plurality of sinogram curves.

10. A non-transmissive computer readable medium storing instructions for execution on a computer system, which when executed by the computer system, cause the computer system to perform the steps of:
    obtaining projection data by scanning an object using the scanning device;
    selecting a projection angle and a fan angle outside a field of view of the scanning device;
    determining, based on the selected projection angle and fan angle, a plurality of sinogram curves, each sinogram curve corresponding to a different image point in the object;
    determining a contribution value for each of the sinogram curves based on the obtained projection data;
    calculating estimated projection data for the selected projection angle and fan angle based on the determined contribution values; and
    storing the estimated projection data,
    wherein the step of determining the contribution value includes interpolating the obtained projection data along at least one of the plurality of sinogram curves.

11. The computer readable medium of claim 10, wherein the step of calculating comprises:
    calculating the estimated projection data for the selected projection angle and fan angle based on a weighted sum of the contribution values for the plurality of sinogram curves.

12. The computer readable medium of claim 10, wherein each contribution value is based on a minimum value of the obtained projection data on the corresponding sinogram curve.

13. The computer readable medium of claim 10, wherein each contribution value is based on boundary values of the obtained projection data on the corresponding sinogram curve.

14. The computer readable medium of claim 10, wherein each contribution value is based on a minimum value of the obtained projection data on the corresponding sinogram curve and on boundary values of the obtained projection data on the corresponding sinogram curve.

15. The computer readable medium of claim 10, further comprising:
    storing a table including minimum values and boundary values of the obtained projection data; and
    said step of calculating includes calculating the estimated projection data using data included in the table.

16. The computer readable medium of claim 13, wherein the boundary values are based on a slope of the corresponding sinogram curve.

17. The computer readable medium of claim 15, wherein the table is a minimum value table, and a peak of the minimum value table is rounded off.

18. A system for estimating projection data, comprising:
    a scanning device configured to obtain projection data by scanning an object;
    a selection unit configured to select a projection angle and a fan angle outside a field of view of the scanning device; and
    a processor configured to
        determine, based on the selected projection angle and fan angle, a plurality of sinogram curves, each sinogram curve corresponding to a different image point in the object,
        determine a contribution value for each of the sinogram curves based on the obtained projection data; and
        calculate estimated projection data for the selected projection angle and fan angle based on the determined contribution values,
    wherein the processor is further configured to interpolate obtained projection data along at least one of the plurality of sinogram curves to determine the contribution value.

19. The system of claim 18, wherein the processor is further configured to calculate the estimated projection data for the selected projection angle and fan angle based on a weighted sum of the contribution values for the plurality of sinogram curves.

20. The system of claim 18, wherein each contribution value is based on a minimum value of the obtained projection data on the corresponding sinogram curve.

21. The system of claim 18, wherein each contribution value is based on boundary values of the obtained projection data on the corresponding sinogram curve.

22. The system of claim 18, wherein each contribution value is based on a minimum value of the obtained projection data on the corresponding sinogram curve and on boundary values of the obtained projection data on the corresponding sinogram curve.

23. The apparatus of claim 18, further comprising:
    a storage unit configured to store a table, the table including minimum values and boundary values of the obtained projection data,
    wherein the processor is further configured to calculate the estimated projection data using data included in the table.

24. The system of claim 21, wherein the boundary values are based on a slope of the corresponding sinogram curve.

25. The system of claim 23, wherein the table is a minimum value table, and a peak of the minimum value table is rounded off.

* * * * *